(12) United States Patent  (10) Patent No.: US 7,575,131 B2
Feinberg et al.  (45) Date of Patent: Aug. 18, 2009

(54) MULTI-COMPONENT DELIVERY SYSTEM

(75) Inventors: Marc Feinberg, Ringoes, NJ (US); Jessica Liberatore, Marlboro, NJ (US)

(73) Assignee: Ethicon, Inc., Somerville, NJ (US)

( * ) Notice: Subject to any disclaimer, the term of this patent is extended or adjusted under 35 U.S.C. 154(b) by 583 days.

(21) Appl. No.: 11/180,352

(22) Filed: Jul. 13, 2005

(65) Prior Publication Data

US 2007/0012724 A1    Jan. 18, 2007

(51) Int. Cl.
B67D 5/52 (2006.01)

(52) U.S. Cl. .................... 222/137; 222/1; 222/135; 222/145.6; 604/82; 604/191; 366/268

(58) Field of Classification Search .............. 222/137, 222/145.5, 145.6, 94, 135, 1; 366/269, 268, 366/181.5, 339, 338, 336, 267; 604/82, 191; 285/921, 360; 403/348, 350, 349, 359.3, 403/359.4
See application file for complete search history.

(56) References Cited

U.S. PATENT DOCUMENTS

| | | | |
|---|---|---|---|
| 2,724,383 A * | 11/1955 | Lockhart | 604/88 |
| 3,826,260 A * | 7/1974 | Killinger | 604/413 |
| 4,060,082 A * | 11/1977 | Lindberg et al. | 604/89 |
| 4,117,551 A * | 9/1978 | Brooks et al. | 366/162.1 |
| 4,538,920 A * | 9/1985 | Drake | 366/181.5 |
| 4,631,055 A * | 12/1986 | Redl et al. | 604/82 |
| 4,735,616 A | 4/1988 | Eibl et al. | |
| 5,225,168 A * | 7/1993 | Khosla | 422/135 |
| 5,489,266 A | 2/1996 | Grimard | |
| 5,752,940 A | 5/1998 | Grimard | |
| 6,349,857 B1 * | 2/2002 | Lepsius et al. | 222/391 |
| 6,547,467 B2 | 4/2003 | Quintero | |
| 6,585,696 B2 | 7/2003 | Petersen et al. | |
| 6,592,251 B2 | 7/2003 | Edwards et al. | |
| 2004/0068266 A1 | 4/2004 | Delmotte | |
| 2005/0027240 A1 | 2/2005 | Fehr et al. | |

FOREIGN PATENT DOCUMENTS

| | | |
|---|---|---|
| EP | 0 292 472 A | 11/1988 |
| EP | 1 498 073 A | 1/2005 |
| WO | WO 2005/018831 A | 3/2005 |
| WO | WO 2005018831 A1 * | 3/2005 |

* cited by examiner

*Primary Examiner*—Frederick C. Nicolas

(57) ABSTRACT

A delivery system is provided for mixing and dispensing a plurality of components and a method for its use. The system includes a first assembly having first and second separate chambers capable of holding first and second components respectively, a second assembly having third and fourth separate chambers capable of holding third and fourth components respectively, and a coupling device for movably coupling the first and second assemblies such that the second assembly is movable relative to the first assembly between a first position wherein the first, second, third and fourth chambers remain isolated from one another, and a second position wherein at least the first and third, and second and fourth chambers are in communication with one another via at least one conduit therebetween.

20 Claims, 7 Drawing Sheets

MULTI-COMPONENT DELIVERY SYSTEM

BACKGROUND OF THE INVENTION

1. Field of the Invention

The present invention relates generally to devices and methods for mixing and dispensing multiple components, and more particularly to such devices and methods having particular application for mixing and dispensing of surgical products.

2. Background Discussion

The use of tissue adhesives or sealants is well known in the medical field, and typically requires the end user to take numerous steps to mix and dispense the various components that make up the sealant. Since stability and sterilization are significant concerns for any such sealants, the individual components that make up the sealant are often packaged separately. This is particularly true when one or more of the components must be refrigerated or frozen, or must be cured by, for example, UV light. Under these circumstances, premixing or improper storage can significantly affect the products shelf life and/or effectiveness. Thus, the end user must mix the individual components, and then quickly apply the mixed product.

Mixing of two components has been achieved in the past by various means including transferring material from one syringe to another, transferring material from several individual vials or the like to a syringe, or by using a mixing bowl and subsequently introducing the mixed material into a delivery device. These procedures are tedious and time consuming. It is also known to mix components from two different syringes or the like by providing a mixing nozzle that mixes together the components from the two syringes as they are dispensed. With these types of devices, the amount of mixing is limited, as is the number of components that can be mixed. U.S. Pat. No. 6,592,251 discloses a device that holds two syringes containing separate components end to end, and allows the components to be transferred from one syringe to the other to achieve continued mixing of the components. This device, however, only permits mixing between two syringes, and is otherwise cumbersome and limited in its application.

Accordingly, what is needed is an improved system and method that facilitates mixing and delivery of multiple components.

SUMMARY OF THE INVENTION

The present invention provides a delivery system having a first assembly having a proximal end region, a distal end region, a first chamber capable of containing therein a first component, a second chamber capable of containing therein a second component, a first channel extending from the first chamber to the distal end region of the first assembly, a second channel extending from the second chamber to the distal end region of the first assembly, and a first coupling element at the distal end region thereof. It further includes a second assembly having a proximal end region, a distal end region, a third chamber capable of containing therein a third component, a fourth chamber capable of containing therein a fourth component, a third channel extending from the third chamber to the distal end region of the second assembly, a fourth channel extending from the fourth chamber to the distal end region of the second assembly, and a second coupling element at the distal end region thereof. The first and second coupling elements are engageable so as to movably couple the first and second assemblies. When the first and second assemblies are so coupled, the second assembly is movable relative to the first assembly to a first position wherein the first and third channels are not in communication with one another, and the second and fourth channels are not in communication with one another, and to a second position wherein the first and third channels are in communication with one another so as to form a conduit between the first and third chambers, and the second and fourth channels are in communication with one another so as to form a conduit between the second and fourth chambers.

Also provided is a method for mixing and dispensing a plurality of components, including providing a first assembly having a proximal end region, a distal end region, a first chamber capable of containing therein a first component, a second chamber capable of containing therein a second component, a first channel extending from the first chamber to the distal end region of the first assembly, and a second channel extending from the second chamber to the distal end region of the second assembly, and providing a second assembly having a proximal end region, a distal end region, a third chamber capable of containing therein a third component, a fourth chamber capable of containing therein a fourth component, a third channel extending from the third chamber to the distal end region of the second assembly, and a fourth channel extending from the fourth chamber to the distal end region of the second assembly. The method further includes removably coupling the first and second assembly together so that the first channel is not in communication with the third channel and the second channel is not in communication with the fourth channel, moving the first assembly relative to the second assembly until the first channel is in communication with the third channel and the second channel is in communication with the fourth channel, mixing the components of the first and third chambers together by passing the components between the first and third chambers via the first and third channels, and mixing the components of the second and fourth chambers together by passing the components between the second and fourth chambers via the second and fourth channels. The method also further includes moving the mixed components into either the first and second chambers or the third and fourth chambers, and dispensing the mixed components contained within the first and second or third and fourth chambers through a dispensing element that mixes the contents of the chambers together during dispensing.

The present invention also provides a delivery system for mixing and dispensing a plurality of components, including a first assembly having first and second separate chambers capable of holding first and second components respectively, a second assembly having third and fourth separate chambers capable of holding third and fourth components respectively, and a coupling device for movably coupling the first and second assemblies such that the second assembly is movable relative to the first assembly between a first position wherein the first, second, third and fourth chambers remain isolated from one another, and a second position wherein at least the first and third, and second and fourth chambers are in communication with one another via at least one conduit therebetween.

Finally, a method is provided for mixing and dispensing a plurality of components, including providing a delivery system including a first assembly having first and second separate chambers capable of holding first and second components respectively, and a second assembly having third and fourth separate chambers capable of holding third and fourth components respectively, movably coupling the first and second assemblies together, and moving the second assembly relative to the first assembly from a first position wherein the first, second, third and fourth chambers remain isolated from one another to a second position wherein at least the first and third, and second and fourth chambers are in communication with one another via at least one conduit therebetween.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described herein in conjunction with mixing and dispensing of surgical sealants and adhesives, it is applicable to other areas as well, surgical or non-surgical, such as industrial and/or construction adhesives or sealants.

Figure 1:
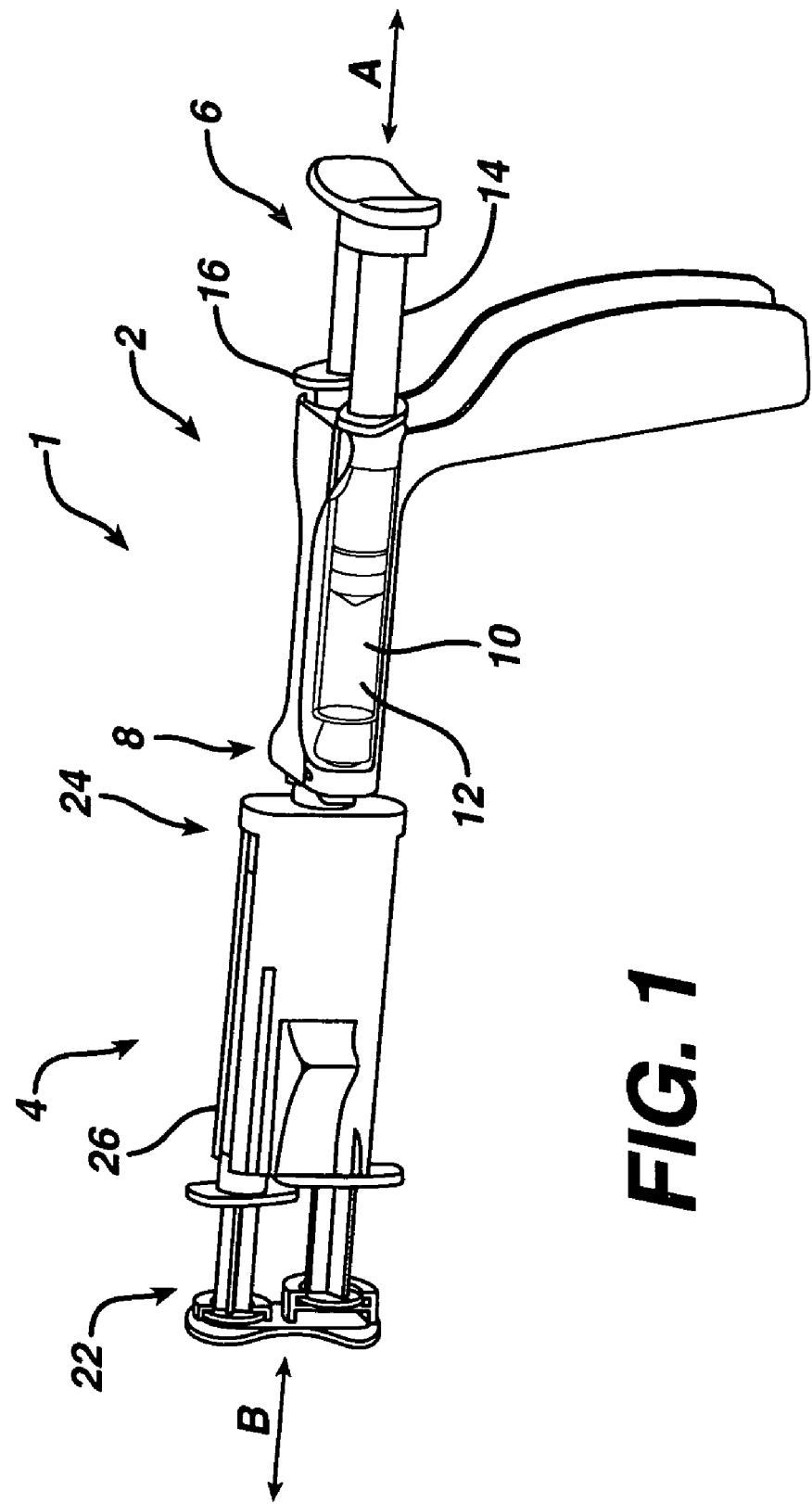
FIG. 1 is a perspective view illustrating one embodiment of a delivery system according to the present invention including a second assembly positioned in a first position relative to a first assembly.
Figure 2:
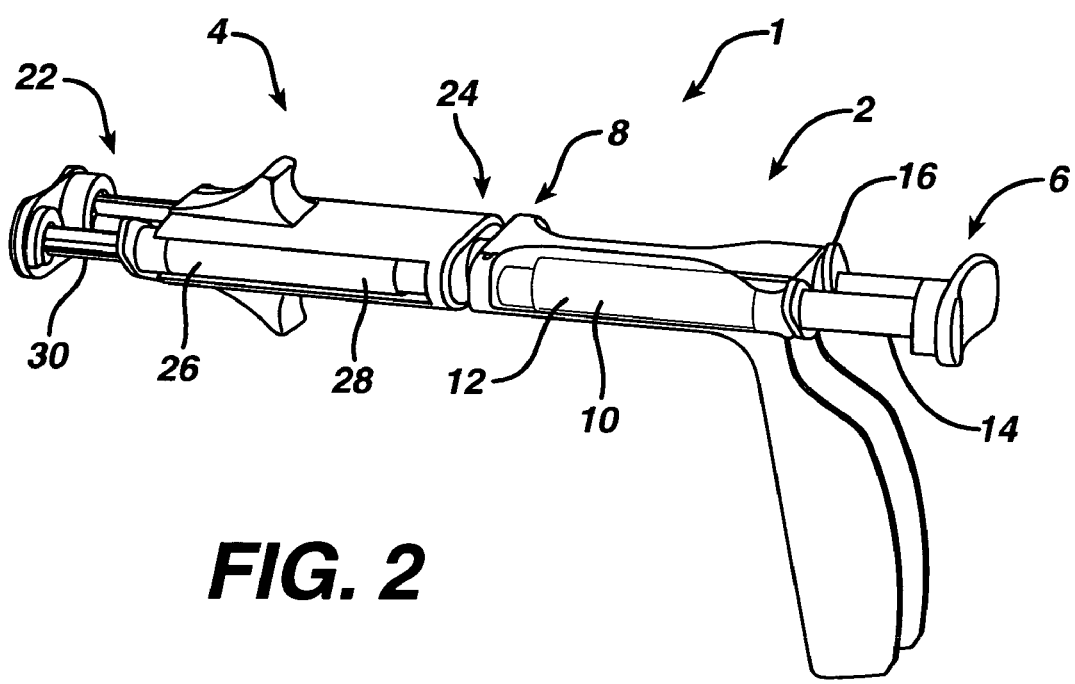
FIG. 2 is a perspective view of the system of FIG. 1 with the second assembly positioned in a second position relative to the first assembly.

Referring now to FIGS. 1 and 2, the delivery system 1 according to the present invention includes a first assembly 2 and a second assembly 4 that are capable of being removably and rotatably coupled to one another as will be described in further detail below. The first assembly 2 has a proximal end region 6 and a distal end region 8, and preferably includes a first syringe like device 10 having a first chamber 12 therein and a first plunger like element 14 that is slidably disposed at least partially within the first chamber 12, and slidable in the directions indicated by arrow A of FIG. 1. The first assembly also includes a second syringe like device 16 having a second chamber 18 therein and a second plunger like element 20 that is slidably disposed at least partially within the second chamber and also movable in the direction indicated by arrow A. The first and second chambers are designed to contain first and second components to be mixed as described further below. Although the term "syringe-like device" is used herein and the illustrated embodiments show an ordinary syringe, various other devices could also be used in accordance with the present invention so long as the component contained within the chamber can be forced in and/or out of the chamber in the manner described further below by an suitable element or device. For example, a flexible storage element that can be compressed to force the component out could be used and is considered to be within the scope of the invention.

The second assembly 4 has a proximal end region 22 and a distal end region 24, a third syringe like device 26 having a third chamber 28 (see FIG. 5) therein and a third plunger like element 30 that is slidably disposed at least partially within the third chamber 28 and slidable in the directions indicated by arrow B of FIG. 1. The second assembly further includes a fourth syringe like device 32 having a fourth chamber 34 therein and a fourth plunger like element 36 that is slidably disposed at least partially within the fourth chamber, and also is slidable in the direction of arrow B. The third and fourth chambers are designed to contain third and fourth components to be mixed.

Figure 3:
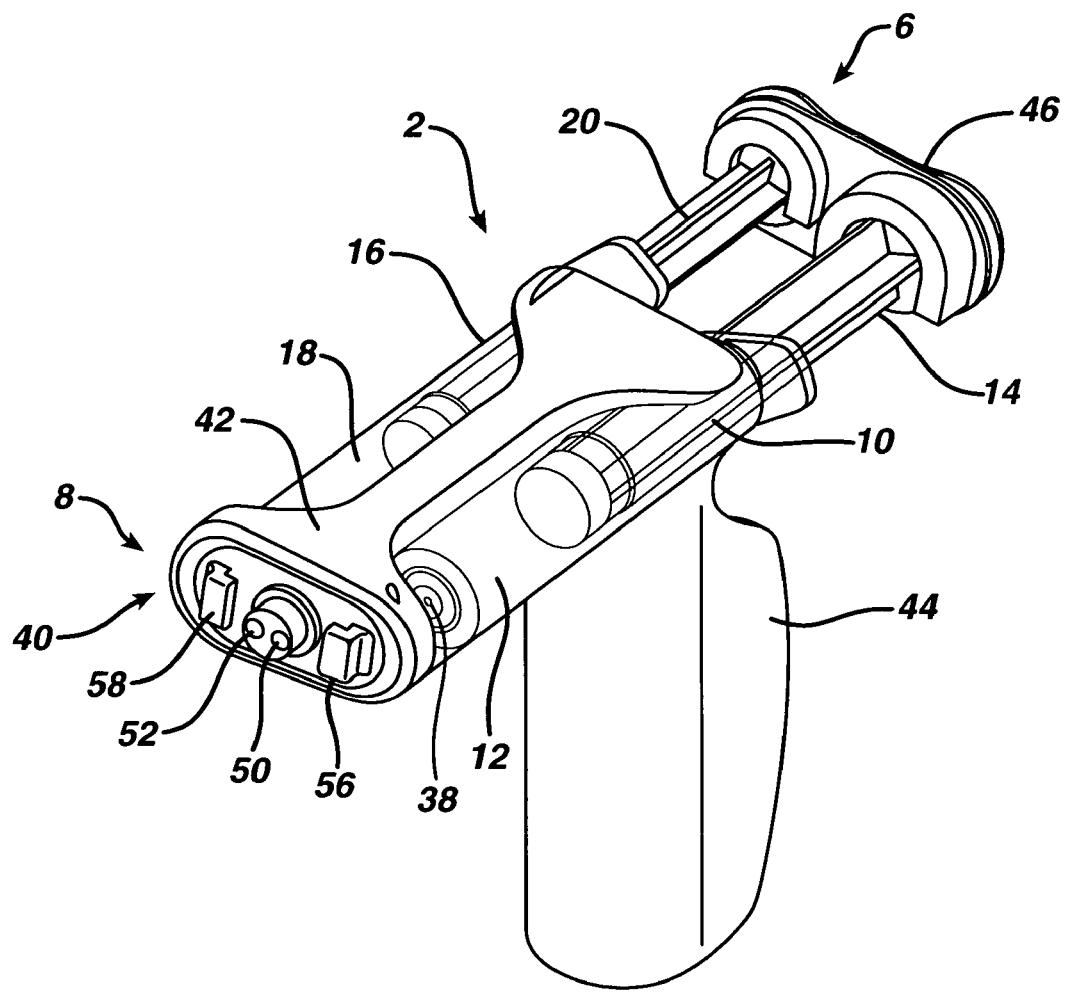
FIG. 3 is a perspective view of the first assembly of the system of FIG. 1.
Figure 4:
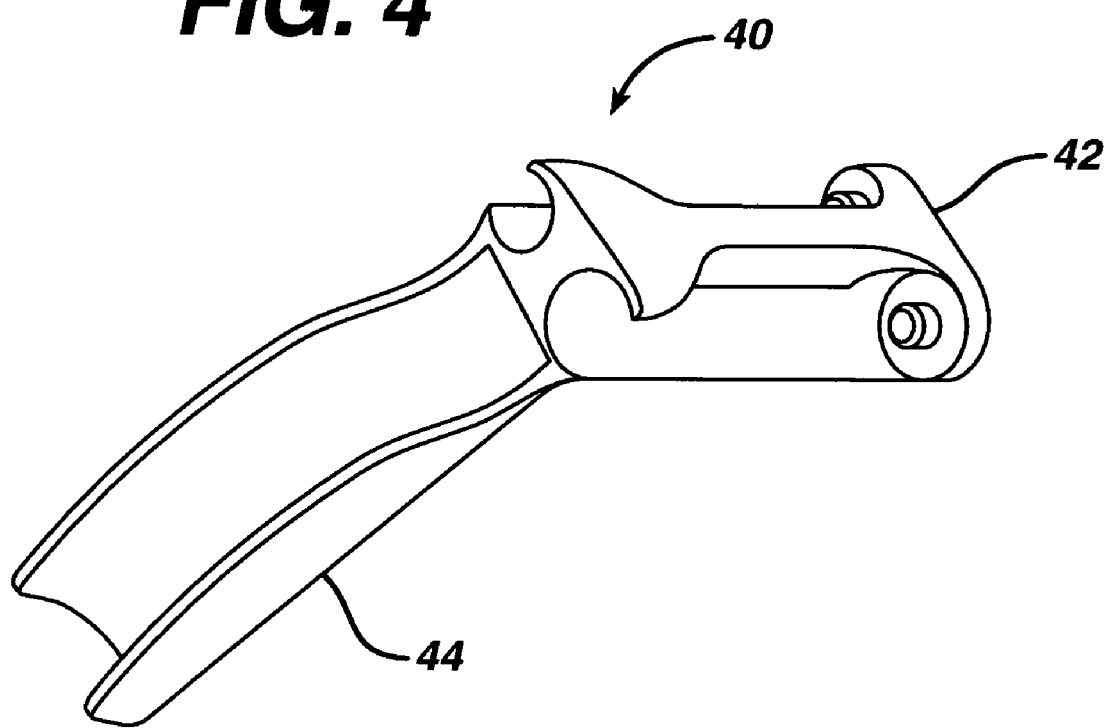
FIG. 4 is a perspective view of the first holding device of the system of FIG. 1.
Figure 4A:
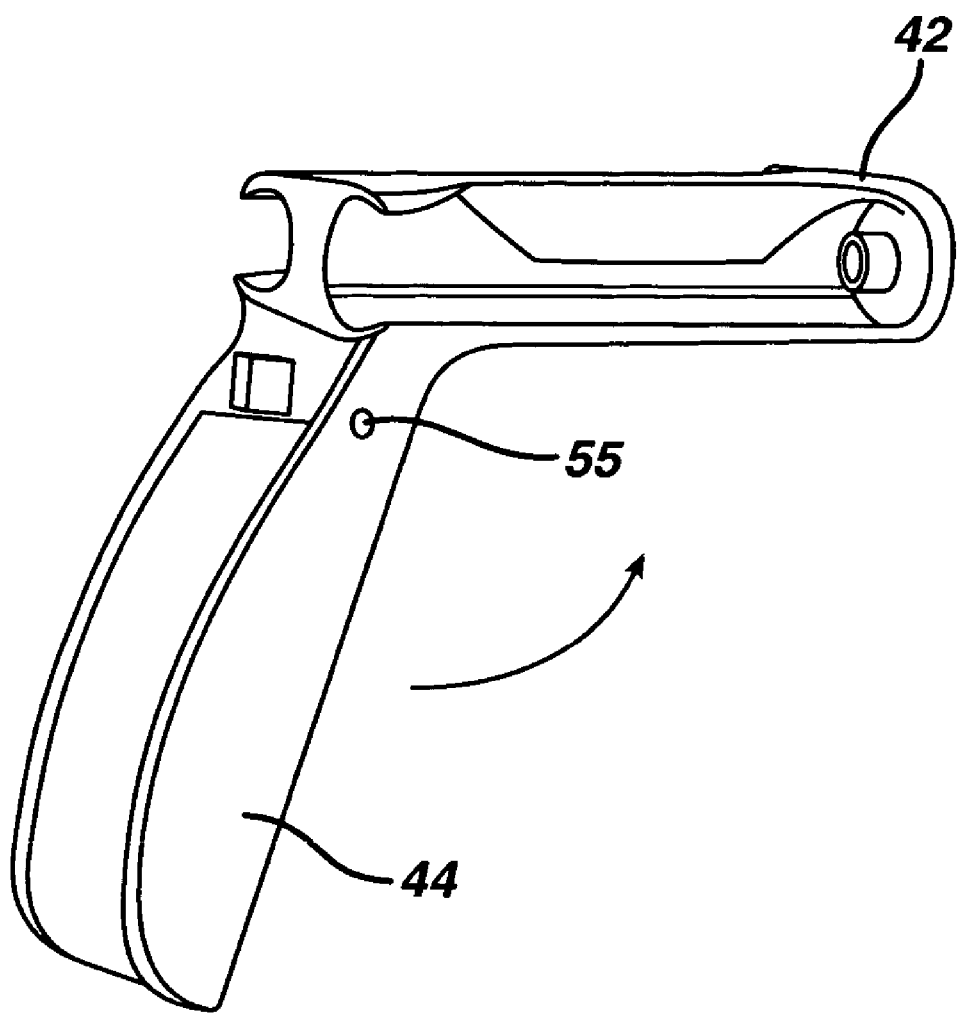
FIG. 4a is a perspective view of an alternate embodiment of a first holding device.

Referring now to FIGS. 3, 4 and 4a, the first and second syringe-like devices 10, 16 are preferably held within a first holding device 40 that preferably includes a first holder 42 and a handle 44 coupled thereto. The first holder 42 and handle 44 may be integral with one another, or may be separate components that are joined together. They may further be pivotally coupled to one another using a pivot pin, hinge or the like 55 such that the handle 44 can be collapsed against the holder 42 in the direction indicated by the arrow in FIG. 4a for more compact packaging. The first and second plungers 14, 20 may also be coupled to a first common actuation member 46 so that movement of the actuation member causes corresponding movement of the first and second plungers at the same time. Finally, positioned at the distal end of the first holding device are first and second retaining members 56, 58 that are engageable with the second assembly as will be described further below.

Each of the first and second syringe like devices 10, 16 have a channel 38 (the channel for second syringe device is not shown, but it substantially identical to that of the first syringe device) at its distal end that extends into the first and second chambers 12, 18 respectively forming a conduit between the first and second chambers and the exterior of the plunger devices, preferably at its distal end. When the first and second syringe devices are positioned properly in the first holding device, these channels are aligned with corresponding channels 50, 52 that extend through a distal end of the first holding device. Thus, through the first and second channels 50, 52 in the holding device and the first 38 and second channels in the first and second syringe devices, the components contained within the first and second chambers 12, 18 can be forced in or out of the respective chambers by movement of the plungers 14, 20.

Figure 5:
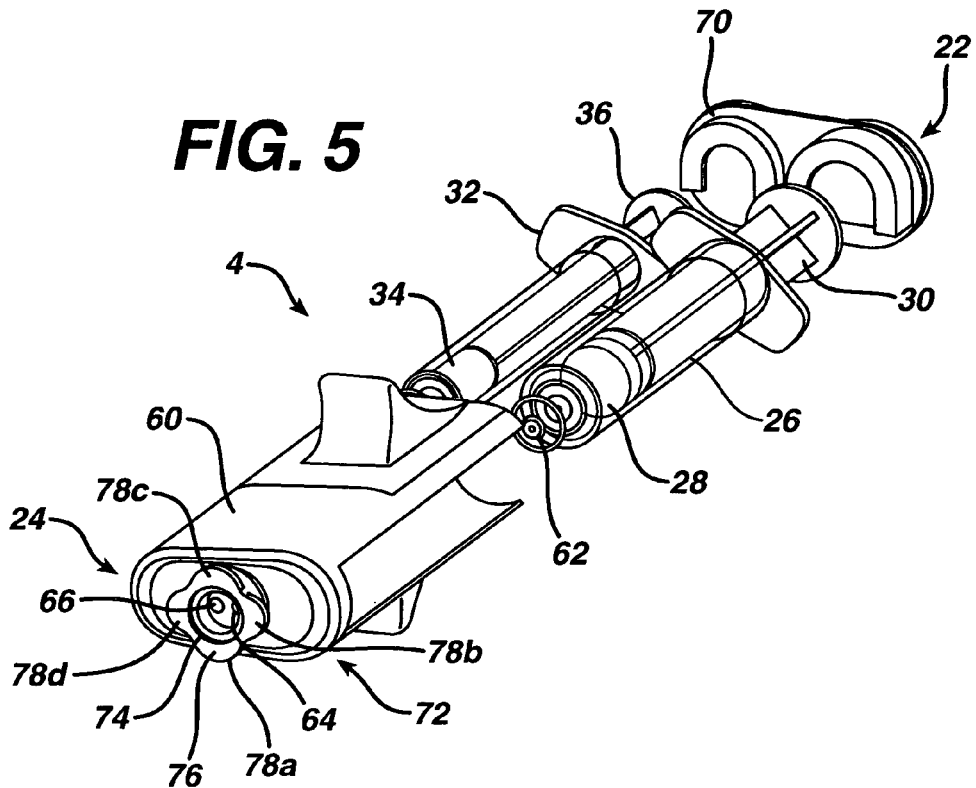
FIG. 5 is a perspective view of the second assembly of the system of FIG. 1.

The second assembly 4 is shown in greater detail in FIG. 5. The second assembly preferably further includes a second holding device 60 within which the third and fourth syringe-like devices 26, 32 are held. As described above in conjunction with the first assembly, the third and fourth syringe devices 26, 32 also include channels 62 (the channel for the fourth syringe is not shown) that extend from the distal end of the syringe device into the third and fourth chambers 28, 34 respectively. The second holding device 60 also includes first and second channels 66, 68 extending therethrough which, when the third and fourth syringe are positioned within the second holding device, are aligned with first and second channels 62 to form a continuous conduit from the third and fourth chambers to the exterior of the second assembly. The second assembly may also include a second common actuation member 70 that is coupled with the third and fourth plungers to enable the plungers to be moved in unison to force fluid or components into and/or out of the third and fourth chambers.

The distal end 72 of the second holding device includes a connection element 74. The connection element 74 is designed to mate with the first and second retaining members 56, 58 of the first holding device. In the illustrated embodiment, the connection element 74 includes a quad lobe connector 76 that includes four projections 78*a-d* around the periphery of the quad lobe connector. The quad lobe connector 76 is designed to engage the retaining members 56, 58 to secure the second holding device to the first holding device, to thereby secure the second assembly to the first assembly. The quad lobe connector is further designed so that the first and second assemblies can be brought together at an angle or approximately 45 degrees relative to one another that is between those shown in FIGS. 1 and 2, and subsequently be removably secured to one another by rotating the second assembly relative to the first assembly to either the first position shown in FIG. 1 or the second position shown in FIG. 2. In these first and second positions (or any position where the first and second assemblies are parallel to one another as in FIG. 2 or perpendicular to one another as in FIG. 1) opposite ones of projections 78*a-d* engage the first and second retaining members 56, 58 so as to removably secure the second assembly to the first assembly. The seal between the first and second assemblies can be further enhanced by cam-action and/or an O-ring feature. The application of force to rotate one of the assemblies can overcome this coupling, and rotate the second assembly to a position wherein the projections do not engage the first and second retaining members, at which time the first and second assemblies can be separated from one another.

Although the illustrated coupling mechanism has been described here in detail, any coupling mechanism may be used that permits movement of the first and second assemblies relative to one another, and that also permits coupling and uncoupling of the first and second assemblies. An important feature, however, is that the first and second assemblies must be movable relative to one another between a first position (i.e., that shown in FIG. 1) wherein the first and second channels 50, 52 of the first assembly are not aligned with (i.e., not in communication with) the first and second channels 64, 66 of the second assembly, and a second position (i.e. that shown in FIG. 2) wherein the first and second channels of the first assembly are aligned with the first and second channels of the second assembly. This feature will be described in more detail below.

As indicated, the first, second, third and fourth chambers described above may each contain a different component that must ultimately be mixed to form the desired surgical adhesive or sealant. For example, in the case of a synthetic, absorbable sealant, the first chamber may contain a polyethylene glycol (PEG) compound and the third chamber may contain a hydroscopic solvent that functions to reduce the viscosity of the PEG. These components are unstable when mixed, and thus it is desirable that they be mixed at the time of sealant application rather than beforehand. The second chamber may contain a catalyst, initiator, or other accelerator that functions to accelerate the cure rate of the mixture. Finally, the fourth chamber may contain an anti-adhesion substance, an anti-microbial or bacterial substance, a pharmacologically active agent, therapeutic biological agents/compositions, or even simply saline.

The system 1 is preferably provided to the user in the configuration shown in FIG. 1, where the first and second assemblies are removably coupled to one another, but are in the first position. Thus, the components within the first and third chambers are isolated from one another, as are the components within the second and fourth chambers. The user would subsequently rotate the second assembly relative to the first assembly to the second position shown in FIG. 2, wherein the first and second channels of the first assembly are now aligned with the first and second channels of the second assembly. This provides a conduit between the first chamber and the third chamber, and a separate conduit between the second chamber and the fourth chamber. Although not shown in the illustrated embodiment, a suitable stop feature may also be added to limit rotation to ensure that only alignment of the first and third, and second and fourth chambers respectively can be achieved.

In the second position, movement of plunger devices 14, 20 or 30, 36 will force the contents of the respective chambers together, and subsequently move them back and fourth between the syringe devices to thereby mix the contents of the first chamber with those of the third, and the contents of the second chamber with those of the fourth. Following sufficient mixing, by further manipulation of the plunger devices, the mixed contents of the first and third chambers are then drawn into the first chamber, and those of the second and fourth chambers drawn into the second chamber. The second assembly is then rotated relative to the first assembly to a point at which none of the four projections 78*a-d* engage the first and second retaining devices 50, 52, and then uncoupled from the first assembly.

Figure 6:
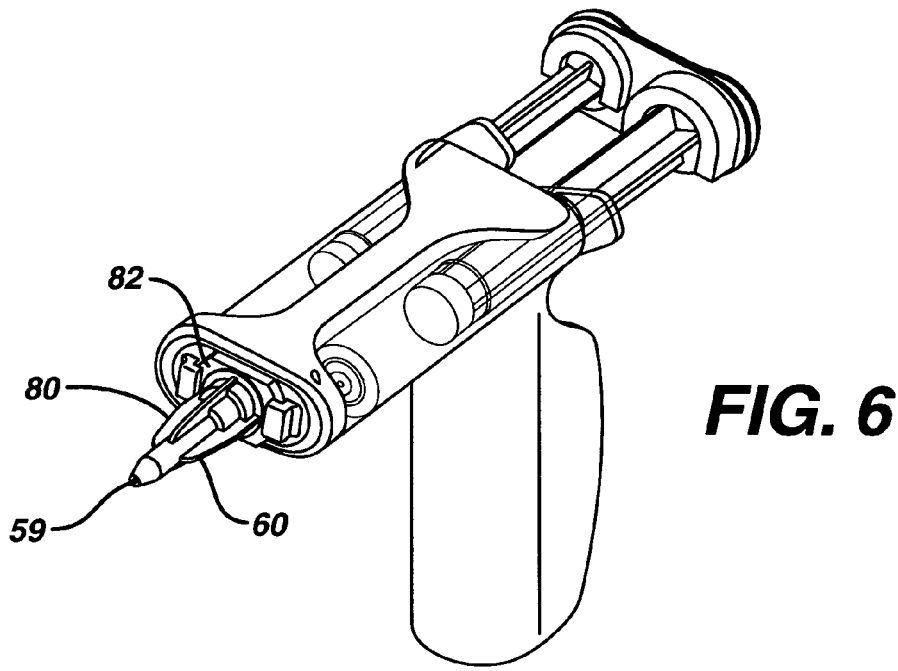
FIG. 6 is a perspective view of the first assembly of FIG. 3 attached to a mixing nozzle.
Figure 6A:
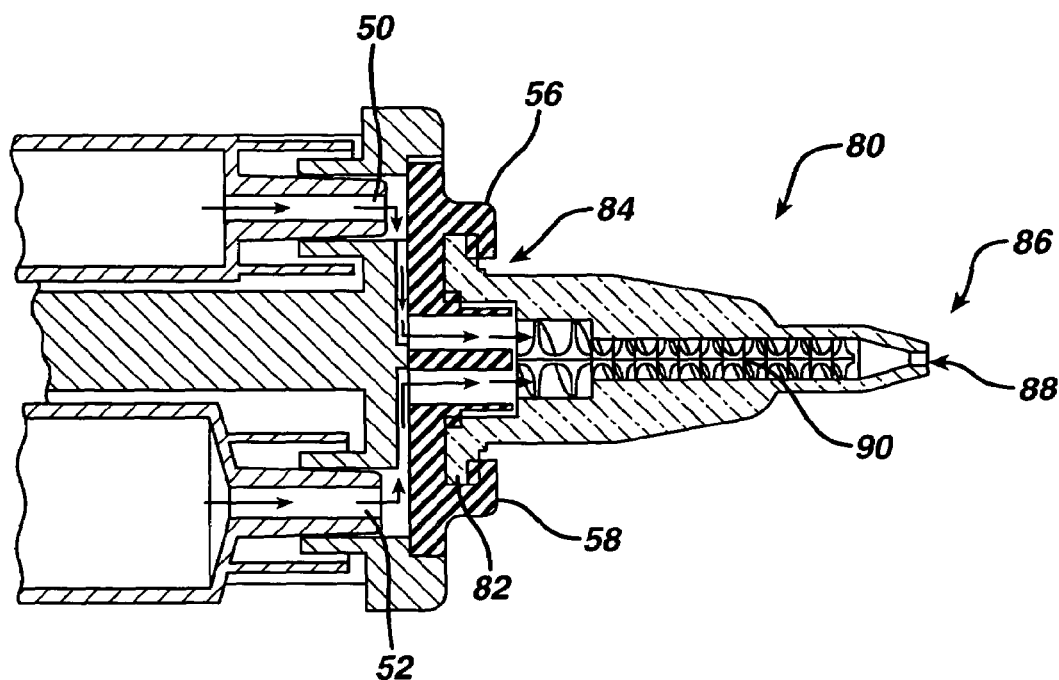
FIG. 6a is a cross-sectional view of the mixing nozzle of FIG. 6.

At this point in time a mixing nozzle 80 is coupled with the first assembly as shown in FIG. 6. The mixing nozzle preferably has a flange 82 extending outwardly at its proximal end that is sized and shaped to engage the retaining members 56, 58 to thereby secure the nozzle to the first assembly. As best shown in FIG. 6*a*, the mixing nozzle has a channel 88 extending through it between its proximal 84 and distal 86 ends. When the nozzle is coupled to the first assembly, the distal end of the channel 88 is in fluid communication with both the first and second channels 50, 52 of the first assembly. The nozzle 80 further includes a motionless mixing element 90, also known as a static mixer, which is well known in the art and consists of internal baffles or the like to mix the two flowable liquids. Thus, when the first and second plungers are forced into the first and second chambers respectively, the mixtures contained therein are both forced out through the nozzle, and are mixed together within the nozzle so that what exits the nozzle is a mixture of the original first, second, third and fourth components. Thus, the present invention enables mixing of up to four discrete components with very little time or effort on the part of the user.

The above description provides details of a preferred embodiment of the invention. Various alternate embodiments will be apparent to those skilled in the art and are also within the spirit and scope of the invention. For example, the interface between the first and second assemblies may include a single conduit that, when the system is in the second position, is in communication with all four chambers. This interface may further include a mixing element similar to that set forth in the mixing nozzle, so that use of the plunger device(s) will move the contents of the first and second chambers to the third and fourth chambers and vice versa, and will mix all components together during this process. Subsequent dispensing of the mixed product could be through a separate mixing nozzle, or through the mixing interface itself, which would further mix the four components together. Accordingly, it is not intended that the invention be limited, except as by the appended claims.

What is claimed is:

1. A delivery system comprising:
a first assembly having a proximal end region, a distal end region, a first chamber capable of containing therein a first component, a second chamber capable of containing therein a second component, a first channel extending from the first chamber to the distal end region of the first assembly, a second channel extending from the second chamber to the distal end region of the first assembly, and a first coupling element at the distal end region thereof;

a second assembly having a proximal end region, a distal end region, a third chamber capable of containing therein a third component, a fourth chamber capable of containing therein a fourth component, a third channel extending from the third chamber to the distal end region of the second assembly, a fourth channel extending from the fourth chamber to the distal end region of the second assembly, and a second coupling element at the distal end region thereof, wherein the first and second coupling elements are engageable so as to movably couple the first and second assemblies, and wherein, when the first and second assemblies are so coupled, the second assembly is rotatable relative to the first assembly to a first position wherein the first and third channels are not in communication with one another and are not axially aligned, and wherein the second and fourth channels are not in communication with one another and are not axially aligned, and to a second position wherein the first and third channels are in communication with one another and are not axially aligned so as to form a conduit between the first and third chambers, and the second and fourth channels are in communication with one another and are not axially aligned so as to form a conduit between the second and fourth chambers.

2. The system according to claim 1, further comprising a means for mixing the components contained within the first and third chambers and the components contained within the second and fourth chambers when the second assembly is in the second position relative to the first assembly.

3. The system according to claim 2, wherein the means for mixing is a plurality of plunger like devices slidably and at least partially disposed within at least the first and second or the third and fourth chambers.

4. The system according to claim 2, wherein the means for mixing is via force applied to the first and second chambers or to the third and fourth chambers.

5. The system according to claim 2, wherein the means for mixing is the application of increased pressure to components contained within at least the first and second, or the third and fourth chambers.

6. The system according to claim 1, further comprising a nozzle having a channel extending therethrough between a proximal end and a distal end, the nozzle being capable of being coupled with the distal end region of the first or second assembly such that, when so coupled, the first and second channels of the first assembly or the third and fourth channels of the second assembly are in communication with the nozzle channel.

7. The system according to claim 6, wherein the nozzle further comprises a mixing element positioned within the nozzle channel.

8. The system according to claim 1, wherein the first assembly further includes a first syringe-like device containing therein the first chamber and including a first plunger-like device slidably disposed at least partially within the first chamber, and a second syringe-like device containing therein the second chamber and including a second plunger-like device slidably disposed at least partially within the second chamber; and the second assembly further includes a third syringe-like device containing therein the third chamber and including a third plunger-like device slidably disposed at least partially within the third chamber, and a fourth syringe-like device containing therein the fourth chamber and a fourth plunger-like device slidably disposed at least partially within the fourth chamber.

9. The system according to claim 8, wherein the first assembly further comprises a first holding element for holding the first and second syringe-like devices.

10. The system according to claim 9, wherein the first holding member includes a holding element and a handle element rotatably coupled to the holding element.

11. A delivery system comprising:

a first assembly having a proximal end region, a distal end region, a first chamber capable of containing therein a first component, a second chamber capable of containing therein a second component, a first channel extending from the first chamber to the distal end region of the first assembly, a second channel extending from the second chamber to the distal end region of the first assembly, and a first coupling element at the distal end region thereof;

a second assembly having a proximal end region, a distal end region, a third chamber capable of containing therein a third component, a fourth chamber capable of containing therein a fourth component, a third channel extending from the third chamber to the distal end region of the second assembly, a fourth channel extending from the fourth chamber to the distal end region of the second assembly, and a second coupling element at the distal end region thereof, wherein the first and second coupling elements are engageable so as to movably couple the first and second assemblies, and wherein, when the first and second assemblies are so coupled, the second assembly is movable relative to the first assembly to a first position wherein the first and third channels are not in communication with one another, and the second and fourth channels are not in communication with one another, and to a second position wherein the first and third channels are in communication with one another so as to form a conduit between the first and third chambers, and the second and fourth channels are in communication with one another so as to form a conduit between the second and fourth chambers wherein the first or second coupling element further comprises at least two projections extending from a periphery thereof, and wherein the other of the first and second coupling elements further comprises at least one retaining element, wherein when the second assembly is in the first or second positions relative to the first assembly, the at least two projections engage the at least one retaining element to thereby couple the first and second assemblies, and wherein the first or second coupling element comprises four projections spaced apart at approximately 90 degree intervals from one another, and wherein the other one of the first and second coupling elements comprises two retaining elements.

12. A method for mixing and dispensing a plurality of components, comprising:

providing a first assembly having a proximal end region, a distal end region, a first chamber capable of containing therein a first component, a second chamber capable of containing therein a second component, a first channel extending from the first chamber to the distal end region of the first assembly, a second channel extending from the second chamber to the distal end region of the second assembly, and a first coupling element at the distal end region thereof;

providing a second assembly having a proximal end region, a distal end region, a third chamber capable of containing therein a third component, a fourth chamber capable of containing therein a fourth component, a third channel extending from the third chamber to the distal end region of the second assembly, a fourth channel extending from the fourth chamber to the distal end region of the second assembly, and a second coupling element at the distal end region thereof;

coupling the first and second coupling elements together so that the first channel is not in communication with and is not axially aligned with the third channel and the second channel is not in communication with and is not axially aligned with the fourth channel;

while the first and second coupling elements are so coupled, rotating the first assembly relative to the second assembly until the first channel is in communication with and is axially aligned with the third channel and the second channel is in communication with and is axially aligned with the fourth channel;

mixing the components of the first and third chambers together by passing said components between the first and third chambers via the first and third channels;

mixing the components of the second and fourth chambers together by passing said components between the second and fourth chambers via the second and fourth channels;

moving the mixed components into either the first and second chambers or the third and fourth chambers; and dispensing said mixed components contained within the first and second or third and fourth chambers through a dispensing element that mixes the contents of said chambers together during dispensing.

13. The method according to claim 12, wherein the first assembly further comprises a first expulsion element capable of forcing the first component out of the first chamber via the first channel and a second expulsion element capable of forcing the second component out of the second chamber via the second channel.

14. The method according to claim 13, wherein the second assembly further comprises a third expulsion element capable of forcing the third component out of the third chamber via the third channel, and a fourth expulsion element capable of expelling the fourth component out of the fourth chamber via the fourth channel.

15. The method according to claim 14, wherein the first, second, third and fourth expulsion elements are plunger-like devices that are slidably positioned at least partially within the first, second, third and fourth chambers respectively.

16. A delivery system for mixing and dispensing a plurality of components, comprising:

a first assembly having first and second separate chambers capable of holding first and second components respectively;

a second assembly having third and fourth separate chambers capable of holding third and fourth components respectively;

a coupling device for rotatably coupling the first and second assemblies such that, while so coupled, the second assembly is rotatable relative to the first assembly between a first position wherein the first and third, and second and fourth chambers respectively remain isolated from one another and are not axially aligned with one another, and a second position wherein at least the first and third, and second and fourth chambers are in communication with one another via at least one conduit therebetween, and are axially aligned with one another.

17. The delivery system according to claim 16, wherein, when in the second position, the first and third chambers are in communication with one another via a first conduit and the second and fourth chambers are in communication with one another via a second conduit.

18. The delivery system according to claim 17, further comprising at least one expulsion device in communication with the first and second and/or third and fourth chambers such that manipulation of the expulsion device forces any components within the first and second chambers into the third and fourth chambers respectively via the first and second conduits.

19. A method for mixing and dispensing a plurality of components, comprising:

providing a delivery system comprising a first assembly having first and second separate chambers capable of holding first and second components respectively, and a first coupling element at a distal end thereof, and a second assembly having third and fourth separate chambers capable of holding third and fourth components respectively, and a second coupling element at a distal end thereof;

rotatably coupling the first and second coupling elements together;

while the first and second coupling elements are so coupled, rotating the second assembly relative to the first assembly from a first position wherein the first and third, and second and fourth chambers respectively remain isolated from one another and are not axially aligned with one another to a second position wherein at least the first and third, and second and fourth chambers are in communication with one another via at least one conduit therebetween, and are axially aligned with one another.

20. The method according to claim 19, further comprising, moving any components within the first and second chambers into the third and/or fourth chamber via the at least one conduit.

* * * * *

UNITED STATES PATENT AND TRADEMARK OFFICE
CERTIFICATE OF CORRECTION

PATENT NO. : 7,575,131 B2
APPLICATION NO. : 11/180352
DATED : August 18, 2009
INVENTOR(S) : Feinberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this

Seventh Day of September, 2010

David J. Kappos
*Director of the United States Patent and Trademark Office*